United States Patent [19]

Oullette et al.

[11] Patent Number: 4,870,829
[45] Date of Patent: Oct. 3, 1989

[54] BIOLOGICAL FREEZING APPARATUS

[76] Inventors: Lucille A. Oullette, 8812 Cockrane Ct., Gaithersburg, Md. 20879; Stephen C. Scott, 1702 Dogwood Dr., Frederick, Md. 21701

[21] Appl. No.: 217,718

[22] Filed: Jul. 11, 1988

[51] Int. Cl.$^4$ .............................................. F25B 19/00
[52] U.S. Cl. ...................................... 62/51.1; 62/78; 62/457.9
[58] Field of Search ................ 62/78, 320, 514 R, 457

[56] References Cited

U.S. PATENT DOCUMENTS

| | | | |
|---|---|---|---|
| 3,233,965 | 2/1966 | McCormick | 62/78 |
| 4,388,814 | 6/1983 | Schilling | 62/78 |
| 4,548,051 | 10/1985 | Moessner | 62/320 |
| 4,751,828 | 6/1988 | Coulter et al. | 62/78 |

Primary Examiner—Ronald C. Capossela
Attorney, Agent, or Firm—Michael W. York

[57] ABSTRACT

Biological freezing apparatus for use on unmodified laboratory liquid cryogen storage container including a specimen holder for holding biological specimens to be frozen and a motor for lowering the specimen holder into the interior of the laboratory liquid cryogen storage containers. An electronic circuit controls the motor so that the specimen holder moves into the interior of the laboratory liquid cryogen storage container at a predetermined desired rate. The specimen holder is constructed of a non-thermally conductive material and this plus its configuration along with the movement of the specimen holder downward at a predetermined rate allows freezing of live biological specimens without doing substantial damage to the specimens.

15 Claims, 4 Drawing Sheets

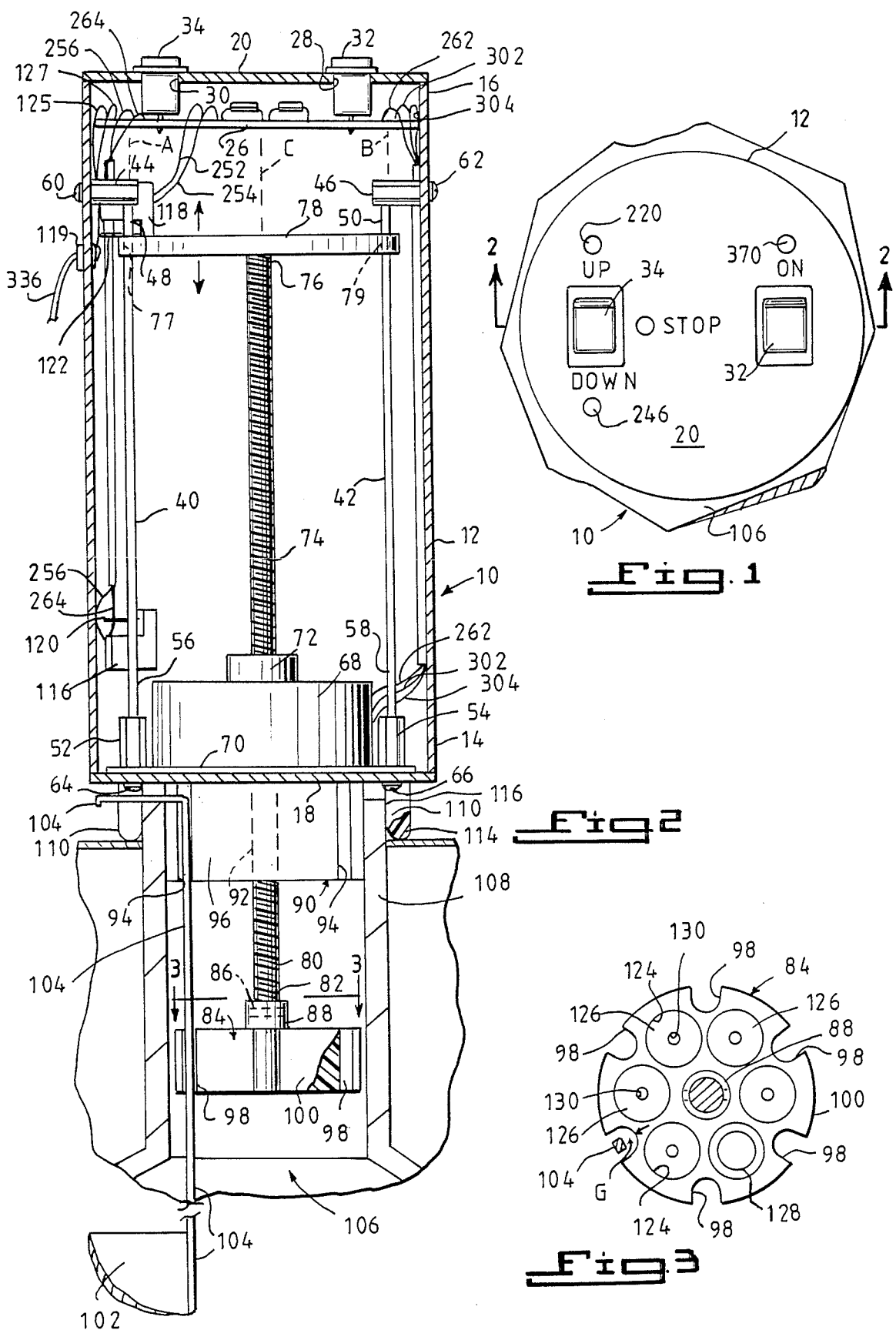

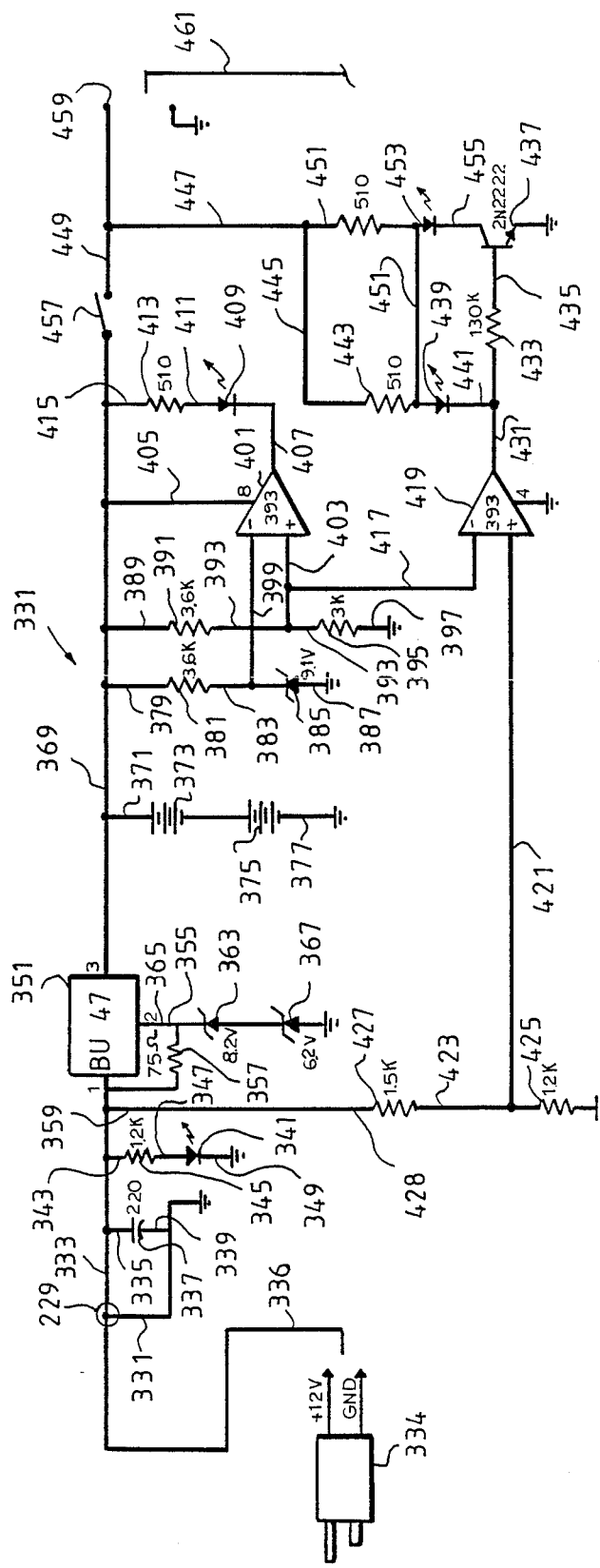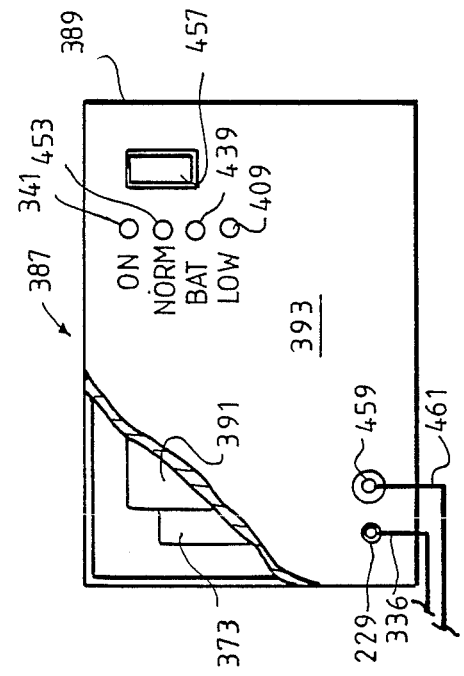
Fig. 6
Fig. 7

BIOLOGICAL FREEZING APPARATUS

BACKGROUND OF THE INVENTION

In biological research and testing it is frequently necessary or desireable that cell cultures and the like be frozen so that they may be used at some future date. In order to be of use at some future date it is necessary that such cell cultures or the like be viable or at least contain a high percentage of viable cells with a good recovery rate when the cells are thawed. Unfortunately, the freezing of cells presents serious problems since improper freezing usually will result in damage to the cells thereby lowering the viability and recovery rate of the cells in the population.

This damage to the cells is caused by too rapid freezing of the cells that results in the formation of ice crystals in the cells because of the water present in the cells. This formation of ice crystals has been known to physically damage the cell walls. This ice crystal formation occurs in the temperature region from about minus five degrees Centigrade to about minus twenty-five degrees Centigrade and hence the manner in which cell cultures are cooled in this temperature zone is highly critical. In order for the cells to survive when passing through this temperature zone it is necessary that the cells be cooled comparatively gradually. It has been reported previously that a minus one degree Centigrade per minute rate is theoretically optimal. This desired cooling rate has been very difficult to achieve. This is made even more difficult by the fact that the common laboratory cooling substance is liquid nitrogen which due to its extremely low temperature tends to cool the cells too rapidly which is not acceptable.

In the past equipment for freezing cell cultures and the like was very complex and expensive and was generally designed to be used for large scale freezing operations. Such equipment in some instances required the use of heating as well as cooling. This equipment is prohibitively expensive for small laboratory use and its size and complexity also make it unsuitable for such use. U.S. Pat. Nos. 4,107,937 and 4,485,641 illustrate such complex apparatus.

There have been other smaller units made available. One of these is illustrated in U.S. Pat. No. 4,377,077. With this apparatus, the cell cultures are placed in a liquid refrigerant and then the entire apparatus is placed in a separate freezer. This requirement for a refrigerant and the use of a separate freezer complicates the use of this apparatus and makes it difficult to use. U.S. Pat. No. 4,388,814 illustrates the use of apparatus for cooling specimens that can use a dewar-type flask which is desireable for small laboratory use. However, a thermally conductive wall must be installed to give proper results. This plus the need to use a temperature sensing device and a controller greatly complicates the apparatus and makes it unsuited for small laboratory use.

This invention overcomes the problems associated with previous biological freezing apparatus. The biological freezing apparatus invention is inexpensive to construct and is simple and easy to use. The invention is well suited to small laboratory use and can be readily used with unmodified dewars and the invention requires no use of a continuous variable controller device.

SUMMARY OF THE INVENTION

This invention related to biological freezing apparatus and more particularly to biological freezing apparatus in which freezing takes place in a manner to avoid extensive damage to the specimens being frozen.

Accordingly, it is an object of the invention to provide a biological freezing apparatus that avoids unduly damaging the biological specimens being frozen.

It is an object of the invention to provide a biological freezing apparatus that effectively freezes biological specimens and the like.

It is an object of the invention to provide a biological freezing apparatus that is easy to operate.

It is also an object of the invention to provide a biologcal freezing apparatus that is comparatively economical to operate.

It is also an object of the invention to provide a biological freezing apparatus that is comparatively easy and economical to manufacture.

It is also an object of the invention to provide a biological freezing apparatus that is particularly suited for use with a comparatively small number of specimens to be frozen.

It is an object of the invention to provide a biological freezing apparatus that is particularly suitable for use by the small laboratory.

It is an object of the invention to provide a biological freezing apparatus that is usable with unmodified laboratory liquid cryogen containers.

It is also an object of the invention to provide a biological freezing apparatus that requires no operational control efforts by the operator.

It is an object of the invention to provide a biological freezing apparatus whose operation is preset to produce the desired biological specimen cooling rate.

It is an object of the invention to provide a biological freezing apparatus that requires comparatively little electrical power.

It is also an object of the invention to provide a biological freezing apparatus that is portable.

It is an object of the invention to provide a biological freezing apparatus that has provisions for supplying uninterrupted power even when there is a power outage.

The present invention provides a biological freezing apparatus for use with an unmodified laboratory liquid cryogen container that includes means for lowering a biological specimen into the liquid cryogen container and preset control means for lowering the biological specimen at a predetermined rate. Specimen holding means are provided for holding the specimens during cooling and for assisting in maintaining a desired cooling rate in which extensive damage to the specimens does not occur.

BRIEF DESCRIPTION OF THE DRAWINGS

The invention will be hereinafter more fully described with reference to the accompanying drawings in which:

FIG. 1 is a top plan view of the biological freezing apparatus invention;

FIG. 2 is substantially a sectional view of the biological freezing apparatus invention taken substantially on the line 2—2 of FIG. 1;

FIG. 3 is a top plan view of a portion of the structure illustrated in FIG. 2 taken substantially in the direction of the line 3—3 thereof;

FIG. 6 is a circuit diagram of an additional embodiment of a backup power circuit for the invention illustrated in FIGS. 1, 2, 3, 4, and 5;

FIG. 7 is a front elevational view of a battery package unit with a portion broken away that contains the circuit set forth in FIG. 6;

DETAILED DESCRIPTION OF THE PREFERRED EMBODIMENTS

Figure 4:
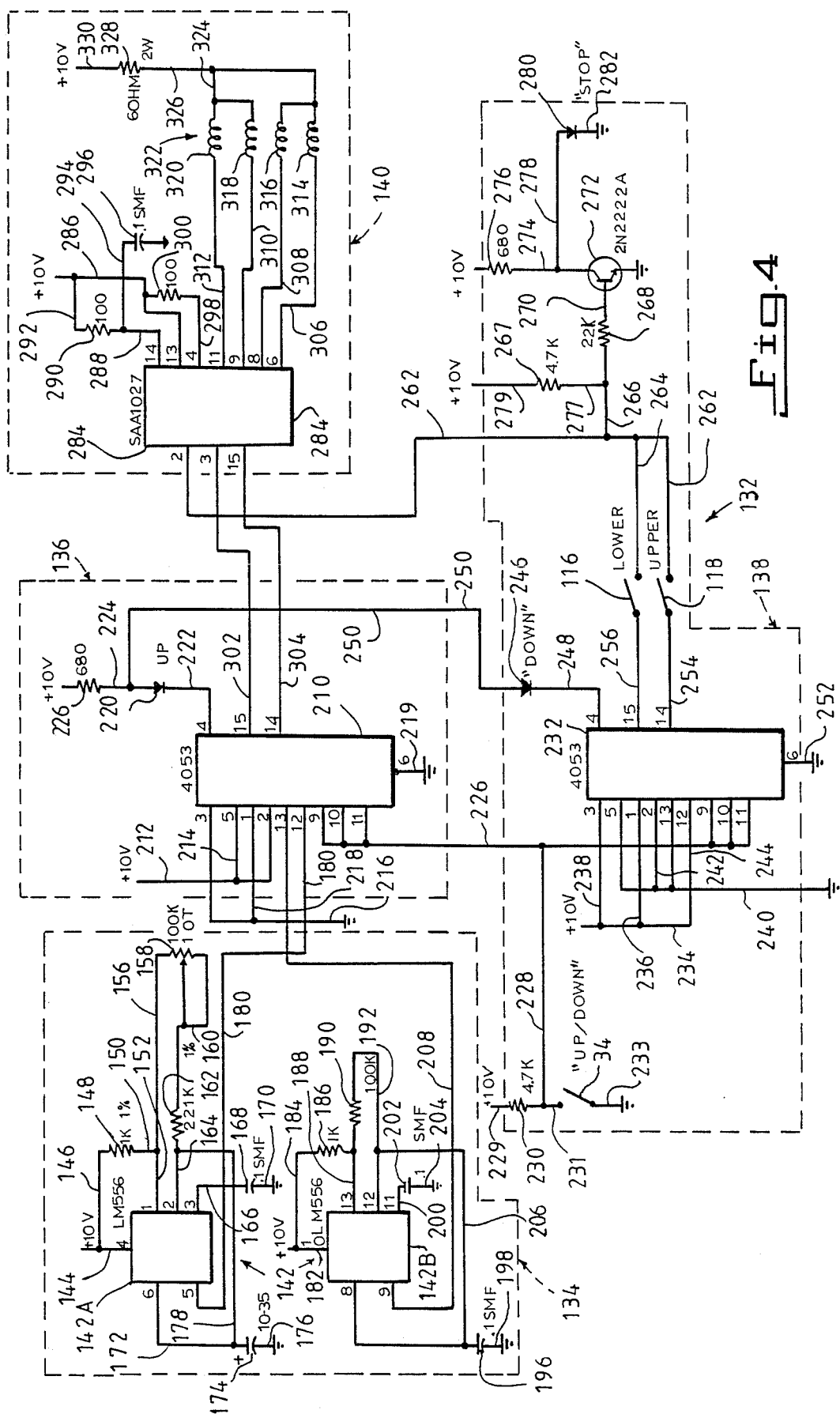
FIG. 4 is a circuit diagram of the electronic circuit that forms part of the invention illustrated in FIGS. 1 and 2.

FIGS. 1 through 3 illustrate the biological freezing apparatus that is designated generally by the number 10. The biological freezing apparatus 10 comprises a generally cylindrical shaped hollow tubular housing 12 whose respective upper and lower end portions 14 and 16 are closed by the respective disc shaped end plates 18 and 20 that are secured to the end portions 14 and 16. A substantially flat disc shaped printed circuit board 26 is located adjacent the end plate 20. This circuit board 26 contains the electronic circuit for controlling the operation of the biological freezing apparatus 10.

The end plate 20 has two generally rectangular shaped apertures 28 and 30 that are sized and shaped to receive and hold the respective electric manually operated switches 32 and 34. As illustrated in FIG. 1, the switch 32 serves as the "On" switch and switch 34 serves as the "Up" and "Down" switch. The switches 32 and 34 are mounted on the circuit board 26 by means known in the art and hence also serve to physically mount the circuit board 26 in place within the housing 12.

Two substantially identical cylindrical shaped guide posts 40 and 42 are located with their long axes lengthwise within the housing 12 and they extend for a substantial length of the housing 12. The guide posts 40 and 42 are mounted within the housing 12 by respective generally cylindrical mounting members 44 and 46 that are connected to the inner wall of the housing 12 and respective inner end portions 48 and 50 of the guide posts 40 and 42 and by generally cylindrical mounting members 52 and 54 that are secured to the respective end portions 56 and 58 of the posts 40 and 42 and the end plate 18. The mounting members 44 and 46 are secured to the housing 12 by means of the respective screws 60 and 62 that pass through the housing and into the mounting members 44 and 46. The mounting members 52 and 54 are secured to the end plate 18 by the respective screws 64 and 66 that pass through the end plate 18 and into the mounting members 52 and 54. The guide posts 40 and 42 are secured in place within the housing 12 so that their respective long axes A and B are substantially parallel.

As illustrated in FIG. 2, a linear stepper motor 68 is located between the end portions 56 and 58 of the guide posts 40 and 42 and is secured in place by having its flange portion 70 bolted to end plate 18 through the previously mentioned screws 64 and 66. The motor 68 has a centrally located rotating portion 72 and an elongated threaded shaft 74 extends through this rotating portion 72. The inner end portion 76 of this threaded shaft 74 is rigidly secured in a manner known in the art to a thin flat substantially disc shaped guide plate member 78. This guide plate member 78 is slideably mounted on the guide posts 40 and 42 by means of the apertures 77 and 79 in the guide plate member 78 that slideably receive the respective guide posts 40 and 42.

In view of this shaft arrangement, the guide plate member 78 can move up and down on the guide posts 40 and 42 as indicated by the arrows, but the guide posts 40 and 42 prevent the guide plate member 78 from rotating. Also since the guide plate member 78 cannot rotate neither can the threaded shaft 74 whose end portion 76 is secured to the central portion of the guide plate member 78. In the preferred embodiment, the long axis of the threaded shaft 74 that is designated by the letter C lies substantially in the same plane as the axes A and B of the guide posts 40 and 42.

The elongated threaded shaft 74 extends completely through the center rotating portion 72 of the motor 68 and a portion 80 of the threaded shaft 74 extends below the motor 68 and housing 12. The end portion 82 of this threaded portion 80 is connected to a specimen holder 84 that is connected to the end portion 82 by means of a pin 86 that extends through an upwardly extending collar 88 in the specimen holder and a hole in the end portion 82. This pin 86 locks the specimen holder 84 to the end portion 82 and prevents any substantial rotational movement between the end portion 82 and the specimen holder 84.

As illustrated in FIG. 2, a substantially cylindrical insulating block 90 is located below the motor 68 on the outside surface of the end plate 18 by bonding the insulating block 90 to the end plate 18 with a suitable epoxy glue or the like. The insulating block 90 has a centrally located aperture 92 that is sized and shaped to receive the portion 80 of the threaded shaft 74. A series of flutes or vertically extending depressions 94 are located at spaced intervals around the curved exterior 96 of the insulator block 90. A substantially similar series of flutes or vertically extending depressions 98 are located at spaced intervals around the curved exterior 100 of the specimen holder 84. The spacing of these depressions 98 is substantially the same as the depressions 94. Both the depressions 94 and 98 are sized and shaped to each receive a portion of a cannister 102 handle. 104 that is used to store samples, etc. in the interior of the liquid cryogen container designated generally by the number 106.

As illustrated in FIG. 2, mounting means are provided on the end plate 18 for mounting the biological freezing apparatus 10 to the opening end portion 108 of the liquid cryogen container 106 comprise three substantially identical resiliently coated projections 110 (only two of which are shown) that project downwardly from the exterior of the end plate 18. These projections 110 are substantially equally spaced around the outer circumference of the end plate 18 and are fastened to the end plate by suitable screws or similar means known in the art. As illustrated, the outer portion of the projection comprises a resilient plastic coating 114 or the like. The purpose of this resilient plastic coating is to exert a gripping force against the adjacently located outer circumferential surface 116 of the opening end portion 108 of the liquid cryogen container 106.

As illustrated in FIG. 2, means for limiting the downward and upward movement of the biological specimen holding means 84 comprising a downward limit switch 116 and an upward limit switch 118 are located on the guide rod 40 and are fixed in place by means known in the art such as by bonding with an epoxy glue or the like. As indicated, the downward limit switch 118 is located near the bottom portion of the guide rod 40 and the upward limit switch 118 is located near the upper end portion of the guide rod 40. It will be noted that the limit switchs 116 and 118 have pressure activated switch members 120 and 122 located to come into contact with the outer portion of the guide plate 78.

The switch member 122 is activated by contact with the guide plate 78 when the biological specimen holder 84 is located in its uppermost position that also results in the guide plate 78 being in its uppermost position since the guide plate 78 and the specimen holder 84 are connected by the threaded shaft 74. In a similar manner, the switch member 120 is activated by contact with the guide plate 78 when the specimen holder 84 is located in its lowermost position since as indicated the guide plate 78 and specimen holder are connected by the threaded shaft 74. The switches 116 and 118 are electrically connected to the circuit board 26 by the respective leads 264, 256, 262, and 254 and the board 26 is electrically connected to the motor 68 and the power input plug 119 by the respective leads 262, 302, 304 and 125, 127.

FIG. 3 illustrates several important details of the specimen holder 84. As illustrated, the specimen holder 84 has six substantially identical generally cylindrical shaped openings 124 located in its upper surface. Each of these openings 124 are closed by a bottom portion 126. The openings 124 are sized and shaped to receive specimen containers such as the container 128. It is important to note that the bottom wall portion 126 has a centrally located hole 130 in it. This hole 130 allows liquid cryogen such as liquid nitrogen to drain from the opening 124 in the event that a liquid cryogen should enter the opening 124.

It has also been unexpectedly determined that this hole 130 assists in the proper freezing of the specimen in the specimen container 128 by allowing it to freeze, but not at such a rapid rate that damage to the specimen is likely to occur. It is suspected that this occurs by allowing liquid cryogen vapor to enter the holes 130. Also, as illustrated in FIG. 3, the vertically extending depressions 98 on the surface of the specimen holder 84 are not only large enough to accomodate the handle 104, but also large enough so that a gap or space designated G also exists between the handle 104 and the adjacent wall of the depression 98. This gap or space G also unexpectedly assists in allowing the proper freezing of the specimen by allowing it to be frozen at a desired rate that is not too fast to avoid damage to the specimen being frozen. This apparently occurs because liquid cryogen vapor enters the area designated by the letter G.

FIG. 4 illustrates the electronic circuit that is used to operate and control the biological freezing apparatus 10 and this circuit is designated generally by the number 132. The electronic circuit 132 comprises a master clock circuit designated generally by the number 134, a direction control circuit designated generally by the number 136, a limit control circuit 138 and a motor control circuit 140 that are all electrically interconnected.

As illustrated, the master clock circuit 134 comprises a type 556 dual timer 142 whose two timing portions are designated 142A and 142B. A +10 volts d.c. is supplied to pin 4 of the timing portion 142A by the lead 144. The +10 volt d.c. source is also connected to pin 1 of the timing portion 142A via respectively the lead 146, the 1K ohm resistor 148, the lead 150 and the lead 152. The lead 152 is connected to pin 2 of the timing portion 142A via the lead 156, the 100K ohm ten turn potentiometer 158, the lead 160, the 221K ohm resistor 162 and the lead 164. Pins 3 and 6 of the timing portion 142A are connected to ground via respectively the lead 166, the capacitor 168, the lead 170, the lead 172, capacitor 174, and lead 176. Lead 164 is also connected to lead 172 by the lead 178. The output of the timing portion 142A is present on pin 5 and on connected lead 180 and comprises substantially 16.667 pulses per minute.

The timing portion 142B has its pin 10 connected to the source of +10 volts d.c. by the lead 182. The 10 volts d.c. is also connected to the lead 184, the 1K ohm resistor 186, the lead 188 that is connected to the pin 13 and the lead 188 is connected to the 100K ohm resistor 190 that is in turn connected to the pin 12 via the lead 192. Pins 8 and 11 are connected to ground via respectively the lead 194, capacitor 196 and lead 198, and lead 200, capacitor 202 and lead 204. The lead 192 is also connected to the lead 194 by the lead 206. The output of the timing portion 142B is present on pin 9 and the connected lead 208 and it comprises substantially 4,000 pulses per minute.

FIG. 4 also illustrates the direction control circuit 136 that is electrically connected to the master clock circuit 134 by the leads 180 and 208. As illustrated, the direction control circuit comprises a type 4053 semiconductor switch 210. The leads 180 and 208 are connected respectively to the pins 12 and 13 of this switch 210. The pin 2 of the switch 210 is connected to the +10 volt d.c. source by the lead 212 as is the pin 5 by the leads 212 and 214. The pins 3 and 1 are connected to ground by the lead 216 and in the case of pin 1 also the lead 218. Pin 6 is also connected to ground via the lead 219. Pin 4 of the switch 210 is connected to the light emitting diode LED 220 via the lead 222 and the LED 220 is in turn connected to lead 224, 680 ohm resistor 226 that is in turn connected to a +10 volt d.c. source. Pins 9, 10, and 11 are connected to lead 226 that is in turn connected to lead 228, 4.7K ohm resistor 230 that is in turn connected to a +10 volt d.c. source via lead 229. The resistor 230 is connected to lead 231 that is connected to "Up/Down" switch 34 that is connected to ground via lead 233.

The limit control circuit 138 in FIG. 4 comprises a type 4053 semiconductor switch 232. As illustrated pin 12 of the switch 232 is connected to a +10 volt d.c. source by lead 234 as are pins 1 and 3 by the additional respective leads 236 and 238. The pins 5, 2, and 13 of the switch 232 are connected to ground by the lead 240 and in the case of pins 2 and 13 the additional leads 242 and 244. Pins 9, 10 and 11 of the switch 232 are connected to the lead 226 and the pin 4 is connected to the light emitting diode LED 246 via the lead 248 and the LED 246 is in turn connected to lead 224 of the direction control circuit 136 via the lead 250. Pin 6 of the switch 232 is connected to ground via the lead 252. The pins 14 and 15 are connected to leads 254 and 256 that are connected respectively to upper limit switch 118 and lower limit switch 116 that are in turn connected to leads 262 and 264 that are connected to lead 266, 22K ohm resistor 268, lead 270 and 2N2222A transistor 272. Lead 266 is pulled to +10 volts d.c. through lead 277, resistor 267 and lead 279. Transistor 272 is connected to lead 274 that is connected to the resistor 276 and a source of +10 volts d.c. The lead 274 is connected via the lead 278 to the light emitting diode LED 280 that is in turn connected to ground via the lead 282.

Also, as illustrated in FIG. 4, the motor control circuit 140 comprises a type 1027 semiconductor chip 284 whose pin 13 is connected to a source of +10 volts d.c. via the lead 286. Pin 14 is also connected to lead 286 via the lead 288, 100 ohm resistor 290 and lead 292. Lead 288 is also connected to ground via lead 294 and 0.1 µF capacitor 296. Pin 4 is connected to lead 286 via lead 298 and 100 ohm resistor 300. Pins 2, 3, and 15 are inputs for the 1027 chip and pins 3 and 15 are connected to respective leads 302 and 304 that are connected to respective output pins 15 and 14 of the switch 210 of the direction control circuit 136. Pin 2 is connected to lead 262 from the limit control circuit 138. The output from the chip 284 is present on pins 6, 8, 9, and 11 and passes via respective leads 306, 308, 310, and 312 to the respective windings 314, 316, 318, and 320 of the stepper motor 322. The stepper motor 322 is in turn connected to a +10 volt d.c. source via leads 324, 326, 6 ohm resistor 328, and lead 330. The resistor 328 limits current to the motor 322 and hence prevents it from damage due o excessive electric current. It should be noted that substantially the entire circuit 132 is located on the printed circuit board 26 in FIG. 2.

Figure 5:
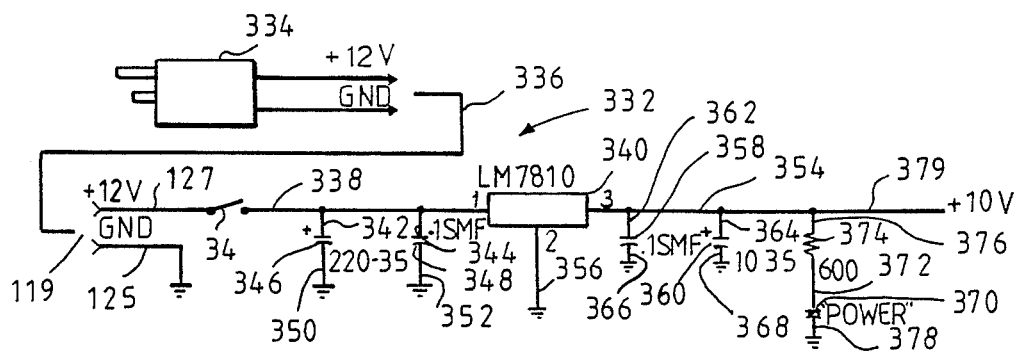
FIG. 5 is a circuit diagram of a further portion of the electronic circuit that forms part of the invention illustrated in FIGS. 1, 2, and 3.

FIG. 5 illustrates the power supply designated generally as 332 for the circuit 132 set forth in FIG. 4. The power supply 332 comprises a standard wall mounted transformer 334 known in the art and is commercially available that converts 120 volts alternating wall current to approximately +12 volts direct current d.c. The approximately +12 volt d.c. output of this transformer 334 is available on the power cord 336 that goes to the power jack 119, the leads 125 and 127 and to the power switch 34. This approximately +12 volts d.c. is then fed on lead 338 to the voltage regulator 340. It should be noted that the lead 338 is connected to leads 342 and 344 that are in turn respectively connected to smoothing capacitors 346 and 348 that are in turn connected to ground via leads 350 and 352.

The regulator 340 takes the approximately +12 volts d.c. input on pin 1 and converts it to +10 volts d.c. on the lead 354 that is connected to pin 3. Pin 2 of the regulator 340 is connected to ground via lead 356. Smoothing capacitors 358 and 360 are connected to lead 354 via leads 362 and 364 and to ground via leads 366 and 368. In order to provide an indication when power is on a power light emitting diode LED 370 is provided that is connected to the lead 354 via lead 372, the 680 ohm resistor 374 and lead 376. The other side of the LED 370 is connected to ground via lead 378. The +10 volt d.c. output on the lead 379 provides the +10 volt d.c. for the circuit set forth in FIG. 4. The entire circuit 332 of FIG. 5 after the leads 125 and 127 through the lead 379 is physically located on the circuit board 26 of FIG. 2.

FIG. 6 sets forth an alternative embodiment for the power supply of FIG. 5. This alternative embodiment is designated generally by the number 331. This backup power supply embodiment 331 also uses the wall mounted transformer 334 and the associated power cord 336. The output from the transformer 334, goes via the power cord 336 to, in this case, the power input jack 299 of the power supply 331 and the lead 333 which is connected by the lead 335 to the smoothing capacitor 337 that is connected to ground by lead 339 and jack ground lead 331. Lead 333 is also connected to the light emitting diode 341 via the lead 343, resistor 345 and the lead 347 and the LED 341 is connected to ground via the lead 349. This LED 341 is on or lighted whenever the transformer 334 is plugged into an electrical circuit. The voltage that would normally be approximately +12 volts d.c. on the lead 333 is fed to the transistor 351 that provides a +14.2 to a +14.4 volt d.c. voltage output on the lead 369 from its pin 3. A resistor 357 is connected from pin 1 to pin 2 of transistor 351 by leads 359 and 365. Pin 2 is connected to ground via lead 355 and two diodes, 363 which is an 8.2 V and 367 which is 6.2 V, which set the output to a nominal +14.3 volts d.c. The output on the lead 369 is from +13.6 to +13.8 volts d.c. depending on the nominal voltagedrop of the diodes 363 and 367.

The lead 369 is in turn connected via lead 371 to the 6 volt batteries 373 and 375, which can be motorcycle batteries or the like, that are connected in series and to ground via the lead 377. The lead 369 is connected to ground via the lead 379, resistor 381, lead 383, Zener diode 385 which sets up a 9 volt reference to compare the low battery voltage of +12.5 volts d.c. and the lead 387 and via the lead 389, resistor 391, lead 393, resistor 395 and the lead 387. The lead 383 is connected via the lead 399 to the negative input of a LM 393 voltage comparator 401, and the lead 393 is connected via the lead 403 to the positive input to the same LM 393 401. The pin 8 of the LM 393 401 is connected to the lead 369 by the lead 405 and the output of the LM 393 401 is connected via the lead 407 to the LED diode 409 that is connected via lead 411, resistor 413 and lead 415 to the lead 369.

The lead 403 is connected via the lead 417 to the negative input to the LM 393 419 whose positive input is connected to the lead 421 that is connected to the lead 423 that is connected via the resistor 425 to ground and via the resistor 427 and the lead 428 to the lead 333. Pin 4 from the LM 393 419 is connected to ground and the output on the lead 431 is connected to the resistor 433, the lead 435 and the base of the 2N2222 transistor 437. Transistor 437 is also connected to ground through the emitter. The lead 431 is connected to the LED 439 via the lead 441 and the LED 439 is connected to the resistor 443, the lead 445, the lead 447 and the lead 449. The lead 447 is connected to the LED 453, the lead 455, and the collector of transistor 437. Lead 451 connects LEDs 439 and 453 at their anodes. A manual switch 457 connects the leads 369 and 449 and the lead 449 is connected to the output jack 459.

The power supply circuit 331 set forth in FIG. 6 functions as follows. With the transformer 334 plugged in electrical voltage is applied to the batteries 373 and 375 to keep them charged and the LED 341 lights to indicate that the power supply circuit 331 is plugged in and is working. In view of the arrangement of the circuit 331 the other LEDs 409, 439 and 453 operate as follows. LED 409 illuminates when the voltage on the batteries has fallen to approximately 12.5 volts. LED 439 illuminates when the operation is from batteries only. LED 453 illuminates when the operation is normal, i.e. power from batteries with constant recharge from the a.c. line.

FIG. 7 illustrates the back up battery pack unit for providing back up or emergency power designated generally by the number 387. This battery pack unit 387 comprises a generally rectangular shaped container or housing 389 that contains the batteries 373 and 375 (only one of which is shown) and substantially the entire power supply circuit 331 set forth in FIG. 6. This circuit 331 is contained on the printed circuit board 391 that is located within the container 389. The container 389, that in the preferred embodiment is made of a suitable metal such as aluminum, has a front face plate 393 that is partly broken away to show the interior of the container 389. The input jack 229 is illustrated connected to the power cord 336 and the output jack 459 is connected to a power cord 461 that is substantially similar to the power cord 336 and the other end of the power cord 461 would be connected to the power input jack 119 (FIG. 2) when the battery pack unit 387 is used.

The LEDs 341, 409, 439, and 453 are located so as to be visable on the face plate 393 where they are arranged in a vertical line with LED 341 on top and the others following downward in the order 453, 439, and 409 to give the respective designated indications from top to bottom "POWER IN", "NORMAL", "BATTERY" and "LOW". These indicator LEDs are to some extent redundant on purpose. This is so since both the LEDs 341 and 453, indicating "POWER IN" and "NORMAL" will be lighted or "on" when the system is operating normally and both will go out or be "off" when line power is lost. The output switch 457 is located immediately adjacent the row of LEDs 341, 453, 439 and 409.

Figure 8:
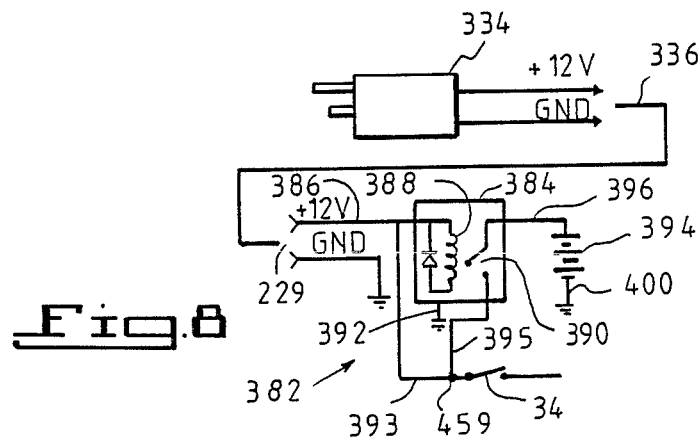
FIG. 8 is a circuit diagram of an additional embodiment of a backup power circuit for the invention illustrated in FIGS. 1, 2, 3, 4 and 5.

FIG. 8 sets forth another embodiment of a power supply circuit designated generally by the number 382. This power supply 382 is generally similar to the power supply 332 except that the relay 384 is interposed just prior to the power switch 34. This relay in the preferred embodiment can be a Teledyne relay series 411 D-12 or a similar relay. This relay 384 functions by normally allowing electrical current to flow on lead 386 through the relay 384 including the relay coil 388 that keeps the switch 390 open. This current then passes on lead 392 to ground. If the current on lead 386 should stop due to interruption of the line current then no electrical current flows through the coil 388 and hence the switch 390 closes and this allows electrical current to flow from the battery 394 via the lead 396, through the switch 390, and on the lead 395 to the switch 34 when the switch is closed. The negative terminal of the battery 394 is connected to ground via the lead 400. In this embodiment, the battery 394, or secondary power supply, is not used until the main power or line current fails. This back up power supply circuit 382 and its battery 394 can be located in a housing similar to that designated 389 in FIG. 7 but provisions for the LEDs 341, 409, 438 and 453 and switch 457 would be omitted since they are not used, but the leads 386 and 393 would be connected to the jacks 229 and 459.

Figure 9:
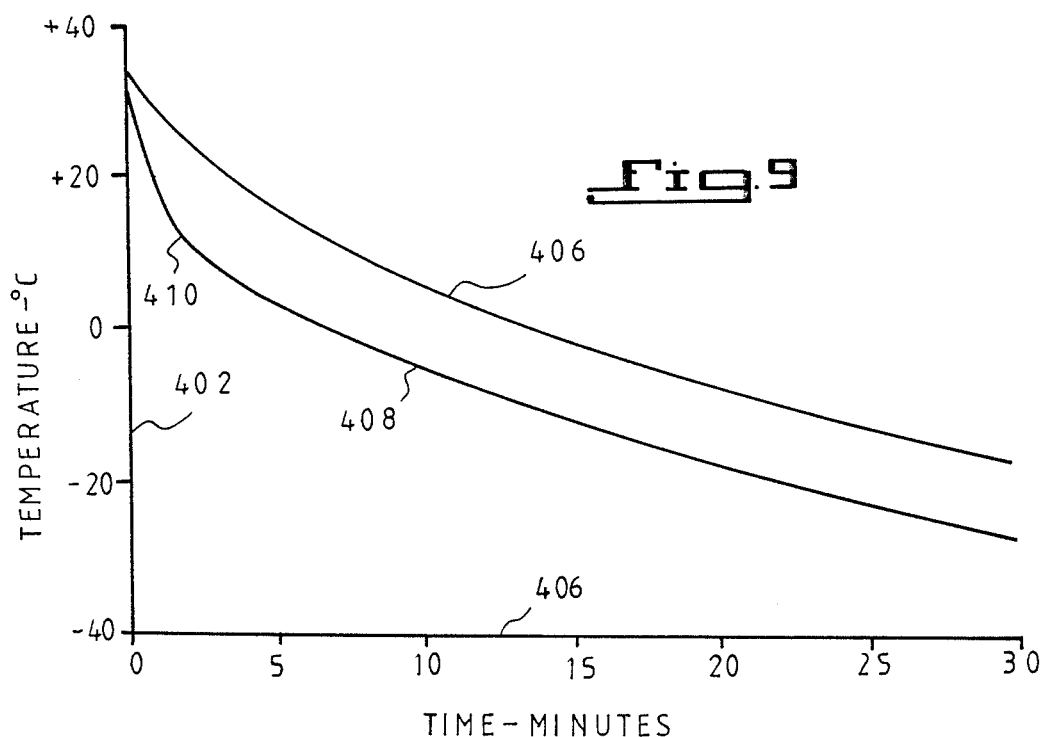
FIG. 9 is a graph setting forth important features of the biological freezing apparatus.

FIG. 9 is a graph of temperature versus time obtained through the use of the biological freezing apparatus 10. As illustrated, the y axis 402 on the graph has temperature in degrees Centigrade and the x axis 404 has time in minutes. The upper graph line 406 is a graph of temperature versus time obtained from a thremocouple (not shown) placed within the specimen holder 84 and inserted into the liquid cryogen container 106 and then lowered through the use of the circuit 132 set forth in FIG. 4. The lower graph line 408 was obtained under the same circumstances except that the specimen holder 84 was removed so that the thermocouple (not shown) was placed in direct contact with liquid nitrogen vapors in the cryogen container 106.

The measurements for the graphs 406 and 408 were taken in an attempt to explain the critical need for the plastic non-metallic specimen holder 84 to prevent too rapid freezing of the biological specimens. As illustrated in FIG. 9, the graph 408 does illustrate lower temperatures than the graph line 406 and the initial portion 410 of the graph line 408 is very steep hence representing a very rapid drop in temperature. However, as reported in U.S. Pat. No. 4,377,077 the critical temperature range for proper cooling is −4 degrees C. to −25 degrees C. and hence the steep drop of the lower graph line 408 occurs at a higher temperatures and time wise prior to such a reported critical temperature range. Consequently, the reason for the critical need for a plastic holder 84 is not completely understood. However, it is clear from tests with a metal holder in place of the holder 84 that a metal holder results in a significant decrease in specimen cell viability after being frozen and hence it is not usable.

The biological freezing apparatus 10 is made and used in the following manner. The tubular housing illustrated in FIGS. 1 and 2 is in the preferred embodiment made from a suitable size aluminum tubing and the end plates 18 and 20 are also made by cutting them from suitable flat aluminum sheet as is the guide plate member 78 that is also suitably drilled to provide the apertures 80 and 82. The threaded shaft 74 is cut from suitable threaded steel rod and the guide posts 40 and 42 are also cut to size from a suitable steel rod. The insulator 90 is cut and machined from a suitable Styrofoam block or the like by means known in the art. The specimen holder 84 is machined from a solid bar of plastic which in the preferred embodiment is called Delrin. The printed circuit board 26 is made by means well known in the art to incorporate the appropriate circuits set forth in FIGS. 4 and 5. The same is true of the circuits such as those designated by the numbers 331 and 382. The biological freezing apparatus 10 is assembled in a conventional manner using standard techniques and fasteners which have been eliminated in places from the drawings for clarity.

The biological freezing apparatus 10 is used in the following manner. One of the power supplies 332, 331 or 382 illustrated in FIGS. 5, 6, and 8 is connected to a suitable source of 120 volt a.c. power. The biological specimen such as that designated 128 is placed within a hole 124 in the specimen holder 84. As illustrated in FIG. 2, the specimen holder 84 is placed within the neck or opening portion 108 of the cryogen container 106 so that the bottom portion of the housing 12 rests on the top of the opening portion 108 of the cryogen container 106 with the projections 110 extending around the exterior of the opening portion 108.

The power switch 32 on top of the housing 12 is then manually pushed to turn it on. As illustrated in FIGS. 5 and 6, this results in +10 volts d.c. being supplied on the lead 354 and this +10 volts d.c. is then supplied to all of the designated +10 volt d.c. inputs set forth in FIG. 4. This +10 volt d.c. input on leads 144 and 182 activate or energize the clock circuit 134 resulting in 16.667 pulses per minute being present on the lead 180 and 4,000 pulses per minute being present on lead 208.

Normally, the specimen holder 84 would be in the "Up" position and consequently, the "Up" LED 220 would be on as would the "Stop" LED 280. The "Up/Down" switch 34 would then be manually activated that connects lead 228 to ground via leads 231 and 233. As a consequence, pins 9, 10, and 11 of the switches 210 and 232 are grounded. This results in the "Up" LED 220 going off and the "Down" LED 246 going on. A signal is provided from pin 15 of switch 210 that is sent on lead 302 to the mode pin 3 on the motor controller 284 that causes the motor 322 to rotate in the down direction. The switch 210 also provides a 16.667 pulses per minute clock signal at pin 14 that is sent on lead 304 to the clock pin 15 of the controller 284 that causes the motor 322 to move the threaded shaft 74 so that the specimen holder 84 moves downward at a rate of one inch an hour for four hours.

When the specimen holder 84 reaches the lowermost position the connected guide plate 78 activates the switch member 120 of the lower limit switch 116. This results in a stop signal being sent on lead 256, switch 116, lead 264, and lead 262 to pin 2 of the motor controller 284 that stops the motor 322. At the same time, the transistor 272 is made inactive and the "Stop" LED 280 comes on. The "Down" LED 246 also is turned on. When it is desired to raise the sample holder 84, the "Up/Down" switch 34 is pushed and this connects pins 9, 10, and 11 of the switches 210 and 232 to ground. This causes an up mode signal to be sent on the lead 302 and a 4,000 pulses per minute signal to be sent on the lead 304 and these cause the controller 284 to have the motor 322 turn on the move the threaded shaft 74 and connected speimen holder 84 in an upward direction.

When the specimen holder 84 reaches its uppermost position, the connected guide plate 78 activates the switch member 122 of the switch 118. This results in a stop signal on lead 262 to the pin 2 of the motor controller 284, the "Stop" LED 280 being illuminated as well as the "up" LED 220 being illuminated. The housing 12 and the connected specimen holder 84 is then manually removed from the liquid cryogen container 106 and the specimen 128 is then removed from the specimen holder 84.

In the event of a loss of normal circuit power to the wall mounted transformer 334, back up battery power is provided by the power supply circuits 331 and 382 of the respective FIGS. 6 and 8 if they are being used. In the case of the power circuit 331 of FIG. 6, the batteries 373 and 375 are always connected into the circuit 132 of FIG. 4 whenever the switch 457 is closed. Consequently, the user would hardly know that the biological freezing apparatus 10 is being battery operated, except that the "Battery Only" LED 439 is illuminated when power is being supplied only by the batteries 373 and 375.

When normal a.c. electrical power is lost with the power circuit 382 of FIG. 8, the battery 394 is then connected automatically into the circuit to supply electrical power to the circuit 132 of FIG. 4. The power circuit 331 has one advantage over the power circuit 382 since the batteries 373 and 375 are always charged which is not the case with the battery 394 in FIG. 8. Consequently, the battery 394 must be periodically checked and charged if necessary.

The 16.667 pulses per minute rate is critical to the proper operational down rate of the motor 322 to provide a proper lowering rate and hence a proper freezing rate for the specimen 128 in the holder 84. Unfortunately, with time electronic components age and this can change this pulse rate. To correct this, change in rate means to compensate for the effects of component aging on the down clock pulse rate of 16.667 pulses per minute comprising the variable resistor 158 is incorporated into the clock circuit 134 and by changing the value of the resistor 158 the pulse rate can be corrected to the desired 16.667 pulses per minute rate.

Unless otherwise stated herein or indicated in the drawings to the contrary, all resistor values are in ohms and all capacitor values are in microfarads.

Although the invention has been described in considerable detail with reference to certain preferred embodiments, it will be understood that variations and modifications may be made to the invention within the spirit and scope of the appended claims.

What is claimed is:

1. Biological freezing apparatus for freezing biological specimens using a liquid cryogen storage container having means for storing samples in the interior of the container including provisions for at least one handle extending into the interior of the liquid cryogen container, said biological freezing apparatus comprising: specimen holding means for holding said biological specimens, said specimen holding means comprising a non-metallic material having a portion thereof sized and shaped to receive a portion of the handle of said sample storing means; mounting means for mounting said specimen holding means in said liquid cryogen storage container; and means for controlling the temperature of biological specimens located in said specimen holding means comprising means for lowering said specimen holding means into said liquid cryogen storage container at a predetermined rate.

2. The biological freezing apparatus of claim 1 wherein the portion of said specimen holding means being sized and shaped to receive a portion of the handle of said sample storing means is of sufficient size to provide a gap between said portion and the adjacent portion of said handle.

3. The biological freezing apparatus of claim 2 wherein said specimen holding means has a plurality of openings for receiving specimens and wherein said openings have an open end portion and a closed end portion.

4. The biological freezing apparatus of claim 3 wherein the closed end portion has a hole located therein.

5. The biological freezing apparatus of claim 4 wherein said means for lowering said specimen holding means into said liquid cryogen storage container comprises a motor.

6. The biological freezing apparatus of claim 5 further comprising thermal insulation located to be between the interior of said liquid cryogen storage container and said motor when said biological freezing apparatus is in the in use position on said liquid cryogen storage container.

7. The biological freezing apparatus of claim 6 wherein said thermal insulation comprises a block having a portion thereof sized and shaped to receive a portion of the handle of said sample storing means.

8. The biological freezing apparatus of claim 5 wherein said means for lowering said specimen holding means into said liquid cryogen storage container comprises means for stopping said lowering at a predetermined lower limit point.

9. The biological freezing apparatus of claim 8 further comprising means associated with said motor for raising said specimen holding means upward from the interior of said liquid cryogen storage container at a predetermined rate.

10. The biological freezing apparatus of claim 9 wherein the predetermined rate for raising said specimen holding means is substantially greater than the predetermined rate for lowering said specimen holding means.

11. The biological freezing apparatus of claim 5 further comprising means associated with said means for lowering said specimen holding means into said liquid cryogen storage container for providing back up battery power to said means for lowering said specimen holding means.

12. The biological freezing apparatus of claim 11 wherein said back up battery power supply means includes at least one battery and further comprising means associated with said back up battery power supply means for indicating the status of said battery.

13. The biological freezing apparatus of claim 5 wherein said mounting means comprises a non-rotatable shaft interconnecting said motor and said specimen holding means.

14. The biological freezing apparatus of claim 5 further comprising means for compensating for component aging operatively associated with said means for lowering said specimen holding means.

15. The biological freezing apparatus of claim 5 wherein further comprising a housing containing said motor and a plurality of resiliently coated projections located on said housing located to exert a gripping force against said liquid cryogen storage container.

* * * * *